United States Patent [19]

Landwehr

[11] 4,370,039

[45] Jan. 25, 1983

[54] METHOD AND APPARATUS FOR PHOTOGRAPHICALLY MEASURING AN OBJECT

[76] Inventor: Ulrich M. Landwehr, Buersche Strasse 4, 4520 Melle 1, Fed. Rep. of Germany

[21] Appl. No.: 208,237

[22] Filed: Nov. 19, 1980

[30] Foreign Application Priority Data

Nov. 29, 1979 [DE] Fed. Rep. of Germany ....... 2948010
Jun. 2, 1980 [DE] Fed. Rep. of Germany ....... 3020901

[51] Int. Cl.³ ...................... G03B 15/00; G03B 29/00
[52] U.S. Cl. .................................... 354/77; 354/120; 354/290
[58] Field of Search .......... 354/77, 110, 118, 120–125, 354/290–292, 209; 356/2

[56] References Cited

U.S. PATENT DOCUMENTS

1,596,458  8/1926  Schiesari ............................... 354/77
4,165,163  8/1979  Lemanski ............................ 354/122

FOREIGN PATENT DOCUMENTS

1034375  7/1958  Fed. Rep. of Germany ...... 354/290

Primary Examiner—John Gonzales

[57] ABSTRACT

A composite photographic picture is generated through double-exposure, whereby the object, as for instance a person, is photographed on one half of the picture whereas a grid pattern is photographed on the other half; for the second exposure, person and grid pattern change position. In each instance of exposure, a line pattern is projected onto the object under utilization of one movable or two fixed, overhung projectors. Equipment is enclosed, permitting easy change of scenery.

13 Claims, 4 Drawing Figures

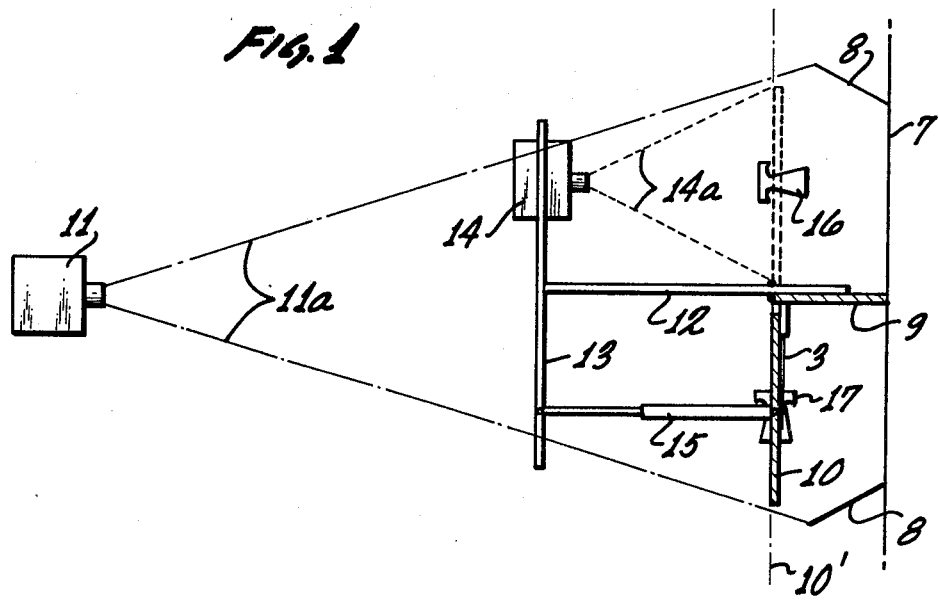
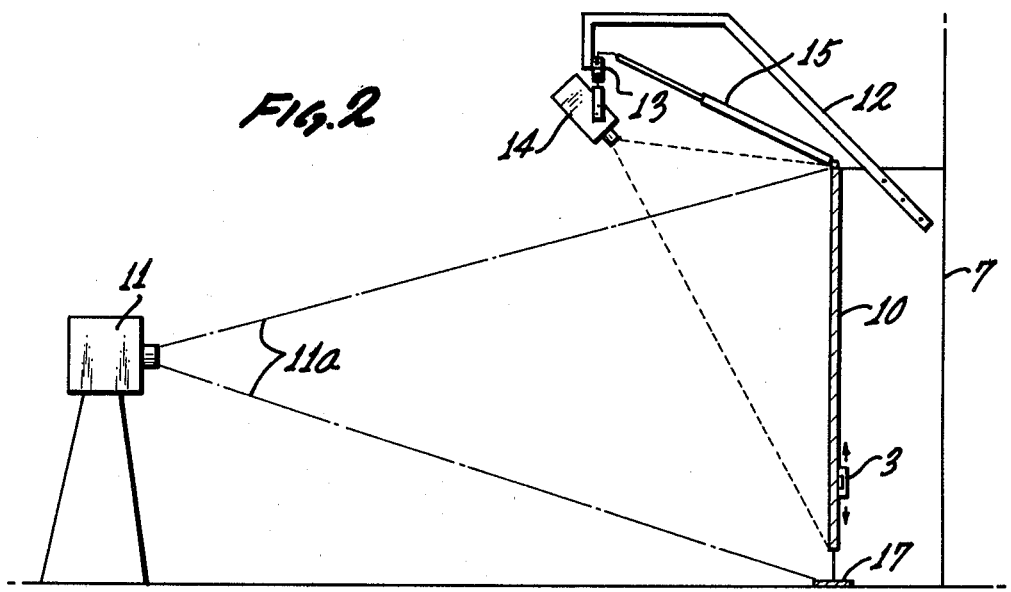

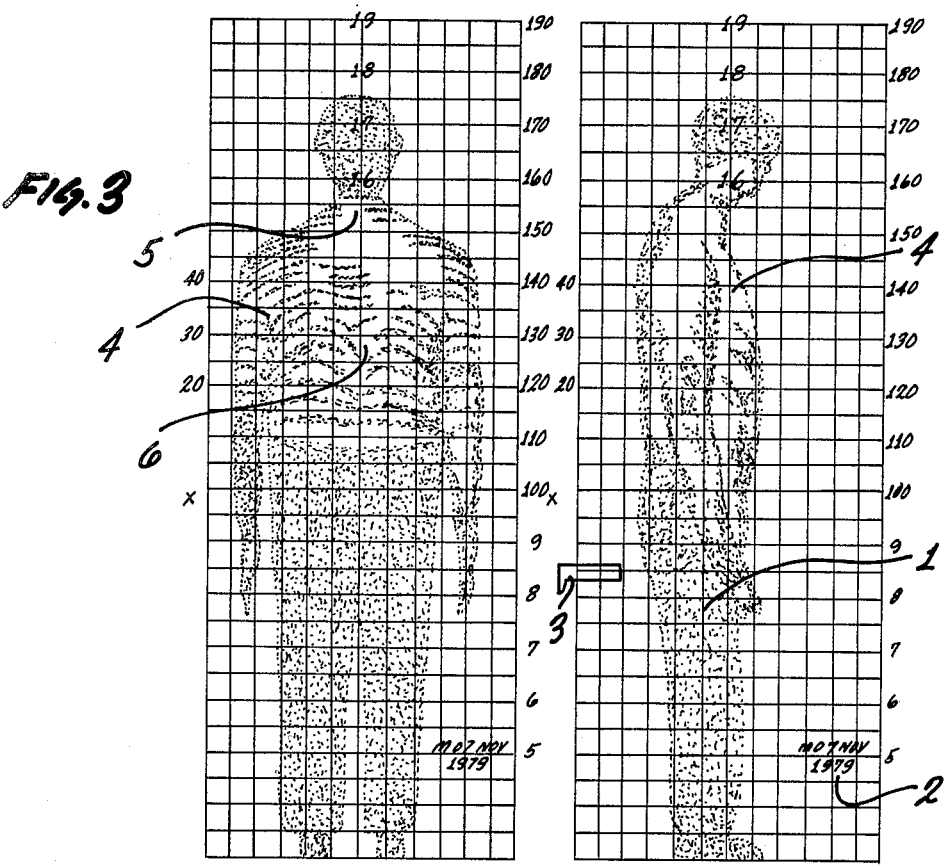
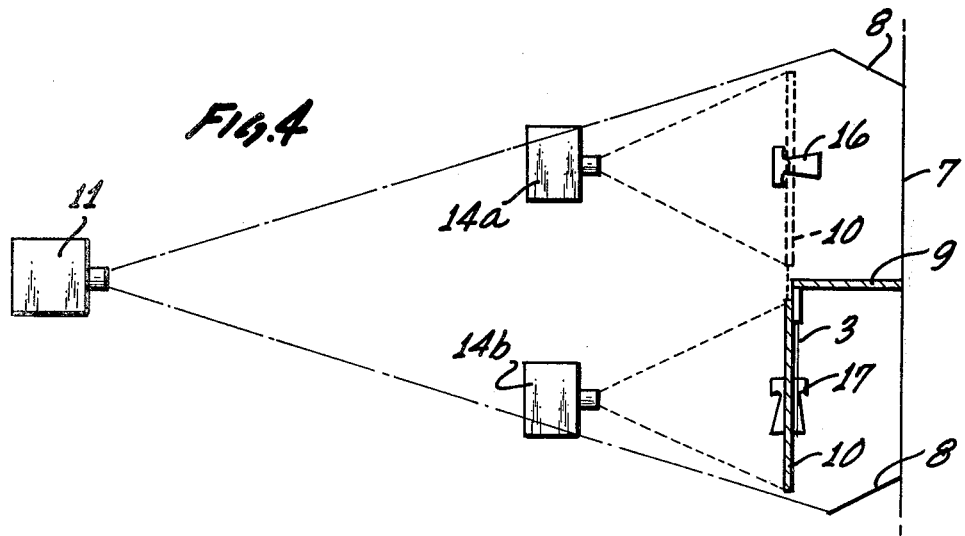

METHOD AND APPARATUS FOR PHOTOGRAPHICALLY MEASURING AN OBJECT

BACKGROUND OF THE INVENTION

The present invention relates to a method of ascertaining photographically the dimensions and measurements of an object; and more particularly, the invention relates to ascertaining such measurements of a person for purposes and in preparation of being clothed.

The German Pat. No. 1,034,375 suggests the following procedure. A picture of a person is taken, together with a measuring tape which is strategically placed in such a way that the scale can be directly referenced to the person. Next, through double-exposure (the camera is not moved, but the person leaves the scene), the image of a scale plate is superimposed. Usually, this procedure is repeated in order to obtain a picture of the person from different directions.

This method is rather time-consuming and expensive. Moreover, the double-exposure requires very accurate handling and manipulation to achieve meaningful results. Also, this method is not well suited to really ascertain details concerning deviations from normal cases, such as a bent spine, a slightly but noticeable extension of the shoulder blade, and so forth.

DESCRIPTION OF THE INVENTION

It is an object of the present invention to provide a new and improved method and equipment for photographically ascertaining measurements (size, dimensions, and so forth) of an object, such as a person.

It is a particular object of the present invention to improve photographic methods in which scale patterns are superimposed upon the image of a person.

In accordance with the preferred embodiment of the present invention, method and equipment of the specific object are improved by projecting a line pattern onto the object (e.g., a person) as it is being photographed; flash light projection synchronized with flash photography being preferred. The lines, as projected, are visible and their distortions delineate surface curvatures of the object.

If the object, e.g. a person, is to be depicted from different angles, it is particularly advantageous to proceed as follows. A camera is directed toward a particular field of view, half of which is occupied, at any particular instance, by a dark plate with a bright grid pattern; the object is placed into the other half, while the line pattern is projected onto that object. A photographic picture is now taken of the entire field of view. Without changing the film frame or plate, the parts are reversed, i.e. the object is placed into the field of view portion previously occupied by the plate while the latter is placed into the other field of view portion. A line pattern is again projected upon the object. As the second one of a double exposure is now taken, the grid image is superimposed upon the previously photographed object, while an image is superimposed upon the previously photographed grid. The result of this is the creation of a single picture, produced by two exposures showing the object twice with superimposed grid and line patterns. The line patterns should be projected centrally onto the object, but from above, and preferably at an angle between 30° and 60° to the vertical. This angular projection, preferably resulting in equidistantly spaced lines when projected onto a vertical plane, is particularly well suited to delineate surface curvatures of the object.

In furtherance of practicing the invention, the field of view may be partitioned physically by a divider to which is hinged a plate carrying similar grid patterns on both sides and covering one half or the other of the field of view, the object being respectively placed in the other half. a single projector may be placed overhead and coupled to that plate so that upon pivoting the plate the projection is repositioned. Use of two projectors, however, is, from the standpoint of accuracy, preferred since they can be maintained in fixed positions.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

FIG. 1 is a top elevation of the equipment for practicing the preferred embodiment of the invention in accordance with the best mode thereof;

FIG. 2 is a side view of the equipment shown in FIG. 1;

FIG. 3 is an example of a photograph made with the equipment shown in FIGS. 1 and 2; and FIG. 4 is the top elevation of a modified example of the preferred embodiment.

Proceeding now to the detailed description of the drawings, the equipment illustrated in FIGS. 1 and 2 includes a wall 7 serving as a neutral or dark background. Mirrors 8 are provided for purposes of obtaining a more uniform illumination of the scene. A vertically oriented divider 9 extends at right angles from the wall, about halfway between the mirrors, and its front end serves as support for a long plate 10. Plate 10 is hinged to the front edge of the divider by means of a hinge frame, permitting pivoting at an angle of, at least, 180° on a vertical axis. The two operating positions of plate 10 are of a nature in which one side or the other is coplanar with a plane 10'.

The plate or wall 10 is basically dark on both sides, and each side carries a square ruling of white, vertical lines and white, horizontal lines. Independently from plate 10, a ruler 3 is also hinged to that divider, for pivoting on a horizontal axis. Moreover, ruler 3 is mounted onto divider 9 in order to permit up and down sliding; but the ruler can be held (e.g., clamped) in an adjusted position.

A camera 11 is positioned at a fixed distance (e.g., three meters) from the wall; the dash-dotted lines 11a denote and delineate the entire field of view of the camera. It can readily be seen that the divider wall 9 divides that field of view into two portions: a left and a right portion. These portions are equal in dimensions. Thus, the camera is positioned in such a way that the optical axis of the lens intercepts the front edge of wall 9. From a different point of view, the space between the background wall 7 and the vertical plane 10', running parallel thereto and through the front edge of divider 9, constitutes a stage and field of view of interest for the camera 11. The width of plate 10 is chosen to cover one-half of that scene or the other, depending upon its position. In FIG. 1, plate 10 covers the right half; upon pivoting at a 180° angle, it will cover the other half. The camera always sees the entire scene, except that, in each instance, one half of the scene is covered by plate 10, but the white ruling lines on the side facing the camera are visible to the camera.

The camera is equipped with a flash light. Moreover, the camera could be of the instant development variety; but it must permit multiple exposure. The scene or theatre stage is further equipped with two stands 16 and 17, defining the exact position a person is to assume on the stage. The stand 16 is constructed in such a way that a person, placing the heels of his (her) shoes against the curved edges, will stand so that his (her) back is, on the average, in that plane 10' delineated by the surface of plate 10 facing the camera when in the alternative position. Analogously, stand 17 has a disposition which permits the spine of a person to run through the plane 10a, coinciding with the other surface of plate 10 in the illustrated position. Of course, a person can only stand in stand 17 when plate 10 has been pivoted out of the way.

An arm 12 extends obliquely up from wall 9 and supports a horizontally running, overhanging rail 13, outside the field of view of the camera. A projector 14 is mounted on a carriage 14a which is suspended from, but runs on, a rail 13 by means of suitable rolls. The projector 14 has a projection lamp which is, however, constructed as a flash light. The camera flash and the projection flash are synchronized with each other.

The projector 14 is shown in a position, in which its projection axis, while pointing downward, is nevertheless situated in a vertical plane which intercepts the stand 16 centrally. Thus, the projection is a central one as far as orientation in the horizontal is concerned. The dashed lines 14a delineate the projection cone. The downward angle of projection is shown to be 45°. Actually, any angle could be used, but one should limit oneself to the range of from 30° to 60° to the horizontal. A 45° angle, however, is clearly preferred.

The projector 14 has an optical system in which the slide side lens is inclined to the optical axis of the projector. Thus, a slide in the projection is imaged in a vertical plane without distortion. The projection is particularly adjusted in order to focus into plane 10a of the surfaces of plate 10 when facing the camera.

The projector 14 is fastened to a belt, or the like, which is also connected to one end of a pair of telescoped rods 15. The other end of these rods is articulated to wall 10. Upon moving plate 10 into the alternative position, that belt or band pulls the projector 14, as shown in FIG. 1, to the right to assume the position in front of the right-hand portion of the scenery in the field of view of the camera. Pivoting of plate 10 causes the rods to be shifted into each other, at first; but subsequently, the rods drag the projector to the left. When the plate is in the alternative position, rods 15 are extended again, and they as well as projector 14 have a disposition which represents the mirror image position of the one shown in FIG. 1; the plane of symmetry coincides with wall 9. The projector runs on the rail via its rolls, and the belt or band drive, slaved to the movement of pivot plate 10, is almost noiseless and actually very simle. Moreover, the belt or band is dimensioned to allow the projector to assume the desired, central positions relative to the left-hand portion or the right-hand portion of the stage whenever one side or the other of plate 10 is coplanar with plane 10a.

As stated, a slide is used for the projection which depicts a line pattern. The line pattern is such that the line images will be equidistantly spaced in plane 10. The line pattern should be selected in accordance with the task at hand. In the present example (a fashion pattern), horizontal lines are clearly preferred. The line pattern could be supplemented by rows of dots, whereby each row has one dot in between two lines. The rows may be spaced by a distance between the twofold and the fivefold value of the line spacing.

As stated, the projector 14 provides a projection zone encompassing one-half of the scene as observed by camera 11. Due to an orientation of the projector in which its axis is inclined at a 45° angle to the horizontal, the line pattern is imaged over the entire height of the scene (FIG. 2) and, for that half of the scene in the horizontal, not covered by plate 10.

The inventive equipment as illustrated permits practicing of the inventive method as follows. Beginning with the setup of the equipment as depicted in FIG. 1, the left-hand scene or the stage is made available. A person may step into stand 16. The right-hand scene is covered by plate 10, the outside grid pattern being visible to the camera.

Camera 11 is now triggered (shutter release), and the two flash lights go off. Accordingly, a line pattern is projected onto the person standing in stand 16 and is photographed therewith. That particular portion covers only one half of the picture. The other half is exposed to the grid pattern on plate 10.

Next, plate 10 is pivoted to cover the left-hand portion of the scene and to expose its other side, also carrying a grid pattern, to the camera. As plate 10 is swung over, tubes 15 are pushed together to some extent and, after more than 90° have been covered by plate 10, it drags the projector into a central position at the other side. The final position is reached when tubes 15 are extended again and have a position at right angles to plane 10a.

Next, the person steps into or onto stand 17, facing sideways. Now, the same film frame or plate in camera 11 is exposed again, the two flash lights being duly triggered. The grid pattern on plate 10 is, thereby, superposed upon the previous back view image of the person, while the side view exposure of the right-hand scene is also double-exposed, on top of the previously photographed grid pattern. Thus, by means of two exposures, one has obtained a front view and a side view of the person; grid patterns are superposed upon both images, and the projected line pattern appears on both pictures of this version. The superposed grid pattern defines directly the scale values of all visible portions of the person, and the projected line pattern establishes, so to speak, a topographic map on the visible surface of the person. A composite picture of this type is shown in FIG. 3. A person is shown in a rear view and in a side view. Grid patterns 1 and 2 of white lines are visible over the entire picture area, although they originated with different sides of plate 10. The lines may have a 1-cm spacing and every fifth line is accentuated. Scale values may be written along the margin of plate 10, which will then be visible on the picture. The lines 1 and 2 of the grids are shown as black lines in the figure for ease of illustration. They are, in actuality, white; the plate background is black to avoid interference with the image of the person upon double-exposure.

Reference numeral 4 refers to the line pattern as projected onto the body of the person. The lines, as curved, delineate body curves. Bunching of the lines near reference numeral 5 represents a slight bend in the upper spine and the neck areas. The picture can now be used for producing patterns for the manufacture of garments, such as trousers, jackets, dresses, coats and so forth. In particular, the picture, including the visible line patterns 4, permits the generation of personalized garment patterns so that material can be cut for a direct and immediate fit. The picture of the back of the photographed person is, in effect, of a nature that permits three-dimensional evaluation. The picture shows also an image of ruler 3 by means of which one can ascertain, e.g., the step length. The line pattern, as projected, permits also ready recognition of any uneven and/or projecting shoulder portions, a bent spinal column, and/or uneven hips. This information is also usable otherwise, e.g. for medical, therapeutic purposes, to monitor objectively any healing progress following injury or illness.

It can readily be seen that only two exposures are needed for two different views of the object (person), and each picture has a superposed grid pattern in addition to a line pattern. This method is, thus, simpler, more economical, and much more accurate than the presently known patterns.

FIG. 4 illustrates a modification which has certain advantages but is more expensive. The equipment here includes two projectors, 14a and 14b, which are mounted in fixed positions, one of each facing the left-hand side and the right-hand side of the stage. The projectors are again mounted at an angle as shown in FIG. 2; they generally have dispositions which are identical to the two operating positions of camera 14 in FIGS. 1 and 2. One may use the same slide for both exposures. Of course, the flash lamps of the two projectors are not triggered at once, but separately for the two exposures. Conceivably, the two stands, 16 and 17, may be provided with weight-responsive switches in order to enable a respective projector flash.

The invention is not limited to the embodiments described above, but all changes and modifications thereof not constituting departures from the spirit and scope of the invention are intended to be included.

I claim:

1. The method of acquiring image information of an object from different sides thereof, comprising the steps of
    placing the object in a first position and in a portion of a field of view of a camera;
    providing a grid pattern next to that object;
    projecting a line pattern onto the object;
    exposing on a film in the camera an image of the object with projected line patterns and next to it an image of the grid pattern;
    exchanging positions of the grid pattern end of the object, the object being oriented at a different angle in relation to the angle of the camera in the exchanged position as compared with the relative position between the camera and the object when the object is exposed as per the exposing step;
    projecting a line pattern onto the object in the exchanged position; and
    exposing the same film strip in the camera to an image of the object with projected line patterns and the grid pattern in the exchanged position.

2. A method as in claim 1, the projected line pattern or patterns being composed of or including horizontal lines.

3. A method as in claim 1, the line pattern being flash-projected in synchronization with the camera's exposure.

4. A method as in claim 1, the line pattern or patterns being projected at an angle of between 30° to 60° to the vertical.

5. A method as in claim 2, the line pattern or patterns as projected being composed of equidistantly spaced lines.

6. A method as in claim 1, wherein the object is placed in such a way that the line pattern is focused onto a surface portion of the object facing the camera.

7. An apparatus of the characteristics described, comprising:
    a photographic camera directed toward a particular field of view;
    a stage means in the field of view;
    a vertical partition centrally disposed on the stage means and having a front edge;
    a plate hinged to said edge and carrying a grid pattern on both sides of the plate provided for covering one half or the other half of the stage means; and
    projection means for projecting a line pattern into the other half or the one half of the stage means not covered by the plate.

8. An apparatus as in claim 7, the projection means including at least one projector having an axis of the projector, being inclined in downward direction.

9. An apparatus as in claim 7 or 8, the projection means including two fixed, mounted projectors.

10. An apparatus as in claim 8, the projection means including a single projector and means for positioning the single projector in front of the one half or the other half of the stage means.

11. An apparatus as in claim 10, the means for positioning including overhung rail means, the projection being movably disposed for running in the rail means.

12. An apparatus as in claim 10, including means for coupling the plate to the projector so that, upon pivoting the plate as hinged, the projector is repositioned therewith.

13. An apparatus as in claim 8, the projector having a corrected lens system which includes a lens closest to a light source of the projector, having its axis inclined to the projector axis.

* * * * *